United States Patent [19]

Ciani

[11] Patent Number: 5,412,319
[45] Date of Patent: May 2, 1995

[54] DEVICE TO DETECT DISTURBANCES IN AN ELECTROMAGNETIC FIELD INDUCED BY SURFACE FAULTS IN A METALLIC BAR OR WIRE ROD IN MOVEMENT

[75] Inventor: Lorenzo Ciani, Udine, Italy

[73] Assignee: Ceda SpA Construzioni Elettromeccaniche e Dispositivi d'Auto-mazione, Buttrio, Italy

[21] Appl. No.: 29,589

[22] Filed: Mar. 11, 1993

[30] Foreign Application Priority Data

Mar. 20, 1992 [IT] Italy ............... UD92A0042
Mar. 20, 1992 [IT] Italy ............... UD92A0043

[51] Int. Cl.⁶ ........................... G01N 27/90
[52] U.S. Cl. ...................... 324/241; 324/242; 324/232; 324/225; 324/262
[58] Field of Search ............... 324/239–241, 324/242, 243, 227, 232, 225, 262

[56] References Cited

U.S. PATENT DOCUMENTS

| | | | |
|---|---|---|---|
| 2,878,447 | 3/1959 | Price et al. | 324/241 |
| 3,484,682 | 12/1969 | Wood | 324/37 |
| 3,518,533 | 6/1970 | Arnelo | 324/40 |
| 3,539,914 | 11/1970 | McClughan | 324/37 |
| 3,582,771 | 6/1971 | Placke | 324/226 |
| 4,785,243 | 11/1988 | Abramczyk et al. | 324/241 |

FOREIGN PATENT DOCUMENTS

| | | |
|---|---|---|
| 0052434 | 10/1981 | European Pat. Off. |
| 0069239 | 6/1982 | European Pat. Off. |
| 0096774 | 5/1983 | European Pat. Off. |
| 0202377 | 9/1985 | European Pat. Off. |
| 0231865 | 1/1987 | European Pat. Off. |
| 0449753 | 3/1991 | European Pat. Off. |
| 2250994 | 11/1974 | France |
| 0696368 | 11/1979 | U.S.S.R. ............... 324/241 |

OTHER PUBLICATIONS

Soviet Inventions Illustrated, Section EI, Week 8407; 28 Mar. 1984; Derwent Publications Ltd. London & SU A-10-12122 14 Apr. 1983 (Abstract).
Patent Abstracts of Japan, vo. 4, No. 7 (C-70) 19 Jan. 1980) & JP A-54-141 368, (Kobe Seikosho) 2 Nov. 1979–Abstract.

Primary Examiner—Sandra L. O'Shea
Assistant Examiner—Jay M. Patidar
Attorney, Agent, or Firm—Antonelli, Terry, Stout & Kraus

[57] ABSTRACT

Device to detect surface faults in a hot metallic bar or wire rod (11) travelling at speeds up to 130 meters per second, the device comprising upstream and/or downstream rough alignment lead-in means (38), in which device are included first coils (29) and at least one pair of second coils (13) coaxial with the first coils (29), the first coils (29) generating an alternating magnetic flow which causes on the surface of the bar (11) parasitic currents that generate in the second coils (13) a magnetic feedback flow, the first (29) and second (13) coils defining a measurement assembly (12), at least two measurement assemblies (12) being included and having their lengthwise axis able to move from an open position defining an intake hole (15), in which the various lengthwise axes coincide substantially with the nominal axis of the feed of the bar (11), to an inspection position defining a resulting inspection hole (15R), in which inspection position the lengthwise axes are substantially parallel to the nominal axis of the feed of the bar (11) and are positioned substantially at an equal distance apart on about a circumference the centre of which lies substantially on that nominal axis of the feed of the bar (11), in which device the index of filling of the resulting inspection hole (15R) is greater than 0.8 and tends to be 0.95 or more, the index of filling being defined by the ratio between the area of the cross-section of the bar/wire rod (11) and the area of the resulting inspection hole (15R).

10 Claims, 2 Drawing Sheets

DEVICE TO DETECT DISTURBANCES IN AN ELECTROMAGNETIC FIELD INDUCED BY SURFACE FAULTS IN A METALLIC BAR OR WIRE ROD IN MOVEMENT

BACKGROUND OF THE INVENTION

This invention concerns a device to detect surface faults in a metallic bar or wire rod in movement.

To be more exact, the invention concerns a device which detects disturbances in the electromagnetic field which are induced by the passage of a hot metallic bar or wire rod, for instance of a hot rolled type passing through a hot rolling mill, within a suitable measurement assembly.

The invention is applied advantageously to the iron and steel industry so as to achieve an automatic detection, in the rolling line, of faults such as cracks, flaking and microflaws on the surface of the hot rolled, drawn or extruded bar or wire rod. The invention can be used for speeds of the rolled stock up to 120–130 meters per second.

The state of the art includes a system for the automatic checking in line of the faults on the surface of substantially round rolled products such as metallic bars of a small diameter or wire rods.

This system makes use of the phenomenon of parasitic currents which are formed on the surface of a conductive body lapped by a variable magnetic flow.

The intensity of these parasitic currents is in proportion to the intensity of the excitation flow and to the surface resistivity of the material.

It is therefore possible to induce, as shown in EP-A-0449753 for instance, by means of an excitation coil an alternating magnetic flow on a metallic bar or wire rod to be inspected; this magnetic flow generates on the surface of the metallic bar a circulation of parasitic currents.

These parasitic currents in their turn produce on receiver coils arranged symmetrically in relation to, and in the vicinity of, the excitation coils a magnetic feedback flow, which, when the metallic bar and the axis of the coils lie substantially on the same axis and there are no faults on the surface of the metallic bar, is perfectly symmetrical in relation to the axis of the bar, to the first excitation coil and to the receiver coils.

If instead the metallic bar contains surface faults in the form of cracks, flaking or microflaws, the unbalancing of the parasitic surface currents entails an unbalancing of the relative feedback flow, which leads to unequal induced voltages.

If one of the two receiver coils is connected to the inverting input of a differential amplifier and the other receiver coil is connected to the non-inverting input of a differential amplifier, a signal of detection of the unbalancing of the feedback flows is obtained at the output of the amplifier.

So as to ensure conditions of maximum sensitivity and maximum uniformity of detection of the device, the element to be inspected has to be fed to the immediate vicinity of the receiver coils so as to minimise the effect of external disturbances which may be produced in the working environment.

This means that the detection head containing the receiver coils should be interchangeable so as to be adapted to the various ranges of diameter of the rolled bar.

Moreover, there is the danger that, if the rolled bar passes very near and contains any deformation, or is subject to an uncontrolled transverse vibration, the bar may be brought into contact with the coils and may cause damage or breakage of the coils or of the bar.

U.S. application Ser. No. 3,518,533 discloses the arrangement of a plurality of coils in series and their displacement in coordination during the passage on the bar to be inspected, so that the coils are brought to the vicinity of the bar; each coil acts on a determined sector of the bar so that all the coils together cover the whole surface to be inspected.

The mechanical displacement system disclosed is substantially unsuitable for bars travelling at the very high speeds usually employed in modern plants, and this leads to faults and inaccurate measurements.

Moreover, this system is substantially arranged for surface inspections of cold metallic wire rods or bars.

In the state of the art the bars are generally passed through the fault detection device substantially without being conditioned laterally apart from a rough alignment.

This solution entails the inability to bring the coils very near to the bar and also the occurrence of disturbances due to the bar being continuously off the axis of the device owing to the parallel traversing of the axis of the bar and to the inclination of the bar.

Instead, it is necessary that the amplitude of the disturbances should be reduced to a minimum so as to ensure a correct and efficient detection of the surface faults by the device.

There is therefore the problem of cancelling or at least restricting these transverse movements and vibrations of the bar in movement, which can lead to disturbances of the field on the receiver coils and may make the bar come into contact with the coils.

EP-A-0231865, EP-A-0096774 and U.S. application Ser. No. 3,582,771 disclose devices for the lateral clamping of bars moving through assemblies performing a non-destructive inspection of the bars. These disclosed devices, owing to their structure, are unable to cooperate efficiently with hot wire rods or bars travelling at a very high speed and are therefore substantially unsuitable for the plants commonly employed nowadays.

SUMMARY OF THE INVENTION

The present applicants have designed, tested and embodied this invention so as to overcome the shortcomings of the state of the art and to achieve further advantages.

The purpose of the invention is to provide a device to detect surface faults in a preferably, but not only, cylindrical hot metallic bar or wire rod being fed at 120–130 meters per second, the device being characterized by great sensitivity and uniform results over a given range of dimensions of the cross section of the bar.

Another purpose of the invention is to embody a means for the lateral clamping and guiding of the bar or wire rod, this means cooperating with the fault detection device in limiting as much as possible and even in possibly preventing any transverse movement or vibration of the bar in relation to the axis of the fault detection device during the surface inspection step.

The detection device according to the invention provides for the employment of at least two, but advantageously three or more, measurement assemblies in line which are installed eccentrically; each assembly comprises at least one coil generating a field and at least one pair of receiver coils differentially connected; all the coils surround the bar to be examined.

These measurement assemblies can be displaced from an open position to an inspection position.

The measurement assemblies in their open position lie substantially on the same axis as each other and as the bar or wire rod being fed and define a large enough entry hole for the passage of bars or wire rods of a given range of diameters, thus lessening the danger that any deformed ends of the bars may touch or damage the detection coils.

The coils in their inspection position are brought very near to the bar to be inspected and are in the best detection position.

The best detection position can be identified by a parameter which can be defined as a filling index calculated as being the inverse of the ratio between the feeding hole for the bar through the detection coils in their inspection position and the dimension of the cross-section of the bar to be inspected.

If the detection is to be effective, the parameter should be greater than 0.7 and tending towards 1.

With the systems of the state of the art it is only possible to fall within this range of the filling index by pre-arranging a specific detection head for each different diameter of the cross-section of the bar to be inspected.

But in view of the problems linked to the transient moment of entry of the leading end of the bar and to the transient moment of the emerging of the trailing end of the bar, the coils of the systems of the state of the art have to have an inner diameter of a given value, so that the filling index is normally located among the minimum admissible values.

Next, if it is desired to work with one set of coils per range of diameters, that range of diameters has of necessity to be small unless it is desired to go below the minimum admissible value of the filling index.

The detection device according to the invention in the inspection position enables the filling index to be kept always among the high values and therefore maintains a very great sensitiveness over a very wide range of diameters.

With the detection device according to the invention in its inspection position it is possible to reach filling index values always greater than 0.8 and tending towards 0.95 and higher.

When the transient moment of entry has passed, that is to say, when the intake of the bar has taken place, each measurement assembly is displaced in different, but coordinated, directions so that the three coils of each single measurement assembly cooperate with a pre-set sector of the perimeter of the bar to be inspected.

For instance, when there are two measurement assemblies, each pair of coils inspects a pre-set half perimeter, whereas if three measurements assemblies are employed, each pair of coils inspects substantially a sector subtending 120°. It is possible to increase the number of measurement assemblies so as to obtain greater values of sensitiveness.

The economically best solution is established by a compromise between the average increase in detection sensitiveness over the range of cross-sections to be covered and the cost and complexity of the device.

The displacement means, which can advantageously but not only be pneumatic, can be pre-set according to the diameter of the bar being processed; the fault detection device can be adapted to a range of diameters without the detection head having to be changed.

Moreover, the fault detection device is characterized by a high speed of change between the open position and inspection position so as to prevent the coils being damaged or broken by a possibly deformed trailing end of a bar during the transient moment of emerging of the bar being fed from the device.

The fault detection device according to the invention cooperates advantageously with a means which clamps and guides the bar and at least reduces considerably any possible vibrations or transverse movements, which might affect the accuracy of the results of the inspection and might lead to contacts between the coils and the bar during the inspection step.

This clamping means consists of at least one pair of opposed idler rolls which define by their positioning the path of the travel of the bar being fed.

This pair of opposed idler rolls is positioned upstream or downstream of the fault detection device, or else two pairs of idler rolls are included, one pair upstream and the other pair downstream of the fault detection device.

These idler rolls are characterized by two positions, an intake position and an inspection position respectively.

The idler rolls in their intake position are kept positioned apart to allow introduction and lengthwise feed of the hot rolled bar.

As soon as the bar has been inserted, the rolls are brought by appropriate actuators to their inspection position alongside the bar being fed.

This situation enables the problems linked to the transient moment of entry of the leading end of the bar and to the transient moment of the emerging of the trailing end of the bar to be obviated.

The speed of change between the intake and inspection positions, in fact, makes it possible to prevent the possibly deformed ends of the bar from touching and damaging the rolls during the transient moments of entry and emerging.

The limit position which can be reached by the rolls is pre-set beforehand according to the diameter of the bar being processed.

According to a variant the actuators possess a reciprocal unbalance of pressure and in this case can put one roll under high pressure and one roll under low pressure. The roll under high pressure is the first to be brought into contact with the bar so as to determine in a definite manner the position of one side of the bar, this position being calculated as being the best for the highest efficiency of the fault detection device.

Thereafter the roll under low pressure is moved and brought into contact with the bar.

The roll under low pressure is positioned in a yielding manner so that its position can be adapted to the variations in diameter of the bar determined by the processing tolerance, thus ensuring a constant pressure exerted by the pair of rolls on the bar. In this way one single point of equilibrium is obtained.

According to a variant the rolls, before being brought to the inspection position, are set in rotation by suitable motors, preferably capable of a characteristic of yielding torque, at a peripheral speed almost the same as the known linear speed of the bar, the direction of rotation being the direction of lengthwise feed of the bar.

In this way the contact between the bar being fed at a high speed and the rolls is made less rough at the moment of closure of the rolls on the bar in the inspection position.

According to a variant the rolls cooperate with a self-alignment system consisting, for instance, of a double rack and a pinion and are displaced with substantially identical but opposite movements.

BRIEF DESCRIPTION OF THE DRAWINGS

The attached figures are given as a non-restrictive example and show some preferred embodiments of the invention as follows.

DETAILED DESCRIPTION OF THE PREFERRED EMBODIMENTS

The reference number 10 in the figures indicates a device which detects surface faults in a bar 11 being fed lengthwise.

Figure 1:
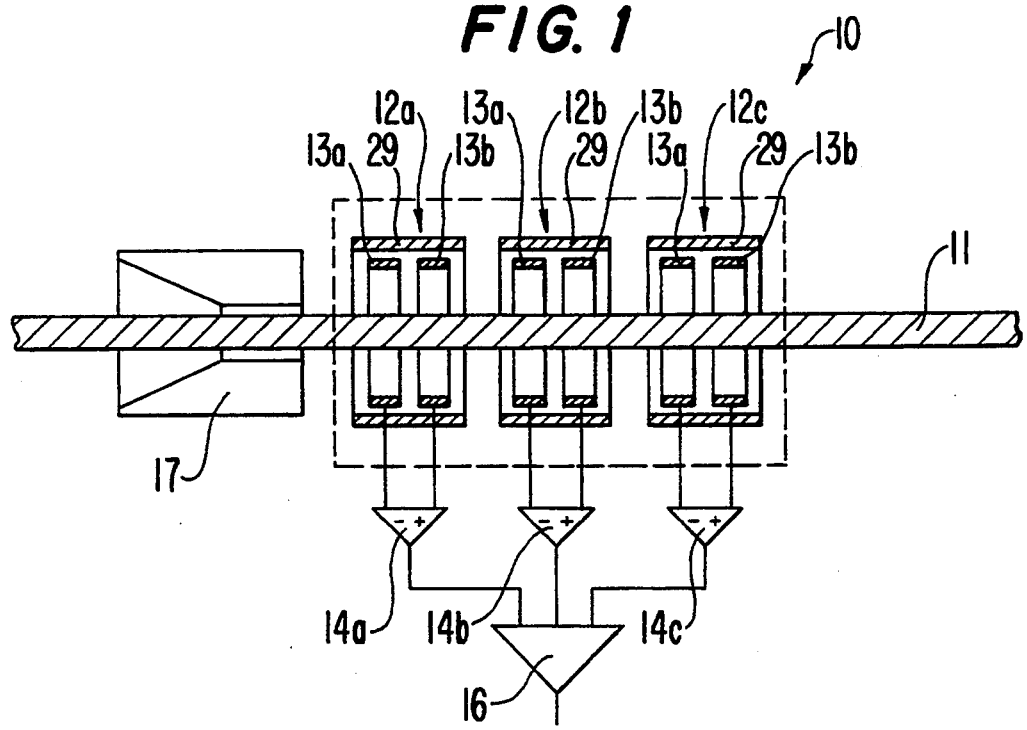
FIG. 1 is a diagram of a lengthwise section of a fault detection device according to the invention.

In the case of FIG. 1 the bar 11 is brought into cooperation with three measurement assemblies 12, respectively 12a, 12b and 12c, each assembly consisting of a first excitation coil 29 and a pair of second receiver coils 13a and 13b, which are substantially on the same axis and in line.

Each excitation coil 29 in each measurement assembly 12 generates an alternating magnetic flow, which induces circulation of parasitic currents on the surface of the bar 11.

The parasitic currents in turn induce a magnetic feedback flow which becomes linked to the respective receiver coils 13a–13b.

The receiver coils 13a and 13b of each measurement assembly 12a, 12b and 12c are connected to their respective differential amplifiers 14a, 14b and 14c, respectively, so that in this example the coil 13a is connected to the inverting input whereas the coil 13b is connected to the non-inverting input, of each respective differential amplifier 14.

Each differential amplifier 14 detects any faults on its respective sector of the bar 11 inspected by its relative measurement assembly 12.

The outputs of the differential amplifiers 14 in turn are connected to a final amplifier 16 which detects the total of the surface faults on the bar 11.

The final amplifier 16 may merely add the three signals received or may evaluate their mean value or may perform other functions such as detecting the greatest of the three signals, for instance.

Figure 2A:
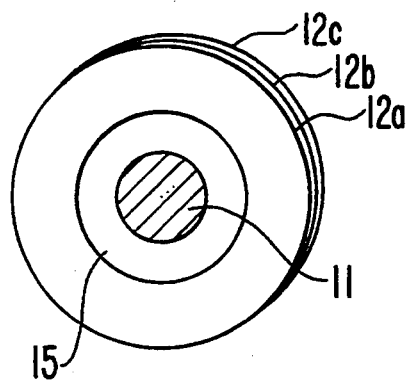
FIGS. 2a and 2b show frontal cross-sections of two steps of the fault detection operation according to the invention.
Figure 2B:
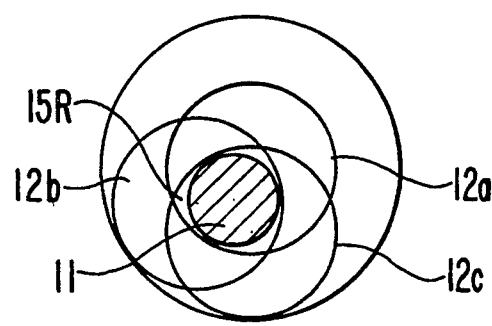

The measurement assemblies 12a, 12b and 12c can be displaced from an open position, in which they may even be concentric or substantially concentric as in FIG. 2a, to an inspection position shown in FIG. 2b.

The lengthwise axis of each measurement assembly 12 in the open position coincides substantially with the lengthwise axis of the other measurement assemblies 12 and coincides substantially with the nominal axis of the feed of the bar 11.

As we said above, the measurement assemblies 12 in their open position lie substantially on the same axis as each other and as the bar 11, so that they define an entry hole 15 which permits a given range of diameters of the bars 11 to pass through the hole 15 without any danger of contact.

Thereafter the measurement assemblies 12 are displaced, and each measurement assembly is brought into cooperation with a pre-set sector, substantially subtending 120° in this example, of the circumference or perimeter of the bar 11.

The lengthwise axes of the measurement assemblies 12 in their inspection position are substantially parallel to each other and to the nominal axis of the feed of the bar 11.

The lengthwise axes in the inspection position (FIG. 2b) are positioned substantially at an equal distance apart and substantially on a circumference, the center of the circumference lying substantially on the nominal axis of the feed of the bar.

The inspection position can be adjusted beforehand according to the diameter of the bar 11 to be processed at the time in question by adjusting suitably the system which displaces the measurement assemblies 12.

It is possible in this way to achieve the best possible filling index and to obtain great sensitiveness and accuracy while maintaining uniform detection over the whole range of diameters compatible with the measurement assemblies 12 in question, since the resulting hole 15R is the best possible.

Figure 3:
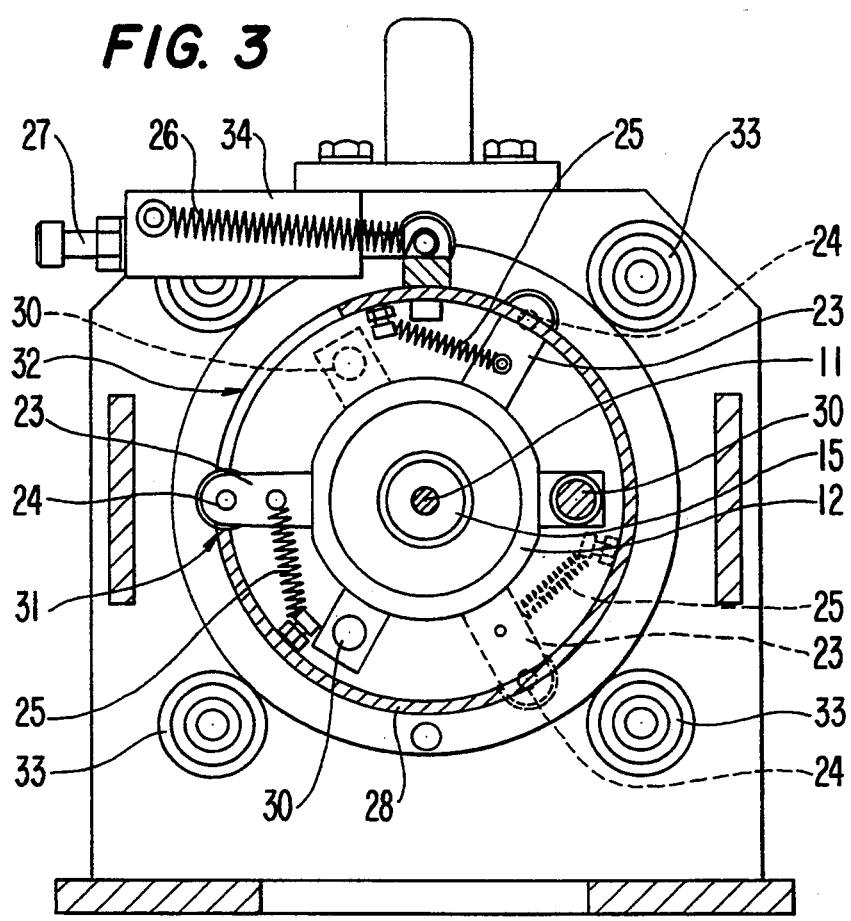
FIG. 3 shows a cross section of a possible embodiment of the invention.

A possible embodiment of the device 10 is shown in FIG. 3, in which there are three measurement assemblies 12 positioned in line in the open position.

In this open position the three measurement assemblies 12 lie substantially on the same axis as each other and as the bar 11 to be inspected and define a large enough hole 15 for the passage of the bar.

Each measurement assembly 12 cooperates by means of its respective projections 23 and rollers 24 with a respective circumferential groove 32 in a circular rotary drum 28.

In this case the roller 24 is kept in contact with a thrust edge 31 of the respective circumferential groove 32 by the action of a respective return spring 25.

Moreover, each measurement assembly 12 can rotate about a stationary pivot 30, which is parallel to the nominal axis of feed of the bar 11. The stationary pivot 30 constitutes the respective centre of rotation of each measurement assembly 12.

The rotary drum 28 can rotate by a determined or determinable angle about the nominal axis of feed of the bar 11, this axis being also the axis of the rotary drum 28 in this example.

The rotary drum 28 is held circumferentially and guided by guide wheels 33.

The desired rotation of the rotary drum 28 is actuated by a jack 34 governed by a travel adjustment means 27 and resisted by a spring 26.

Rotation of the rotary drum 28 sets each measurement assembly 12 in rotation about the stationary pivot 30; contact between each respective roller 24 and the respective thrust edge 31 is ensured by the respective return spring 25.

Thus each measurement assembly 12 is brought with a movement of closure, such as the movement of closure of a camera shutter in this example, to the vicinity of a determined sector subtending 120° of the circumference of the moving bar 11, thus making possible an efficient and accurate detection of surface faults.

When the inspection step has ended, the action of the spring 26 by itself or in cooperation with the jack 34 causes a return to the open position. The jack 34 may be actuated pneumatically, hydraulically, electrically, with a combined system, etc.

According to a variant which is not shown in the figures the detection device 10 is pre-arranged to actuate the measurement assemblies 12 in a linear manner with a sliding movement like a drawer.

The detection device 10 includes pre-adjustment means, which consist, in this example, of the spring 26 and travel adjustment means 27, so as to adjust the positions of maximum approach of the measurement assemblies 12 to the bar 11 in such a way that it is possible to adapt the detection device 10 swiftly to the range of diameters of the bars 11 for which the receiver coils 13 have been produced.

Figure 4:
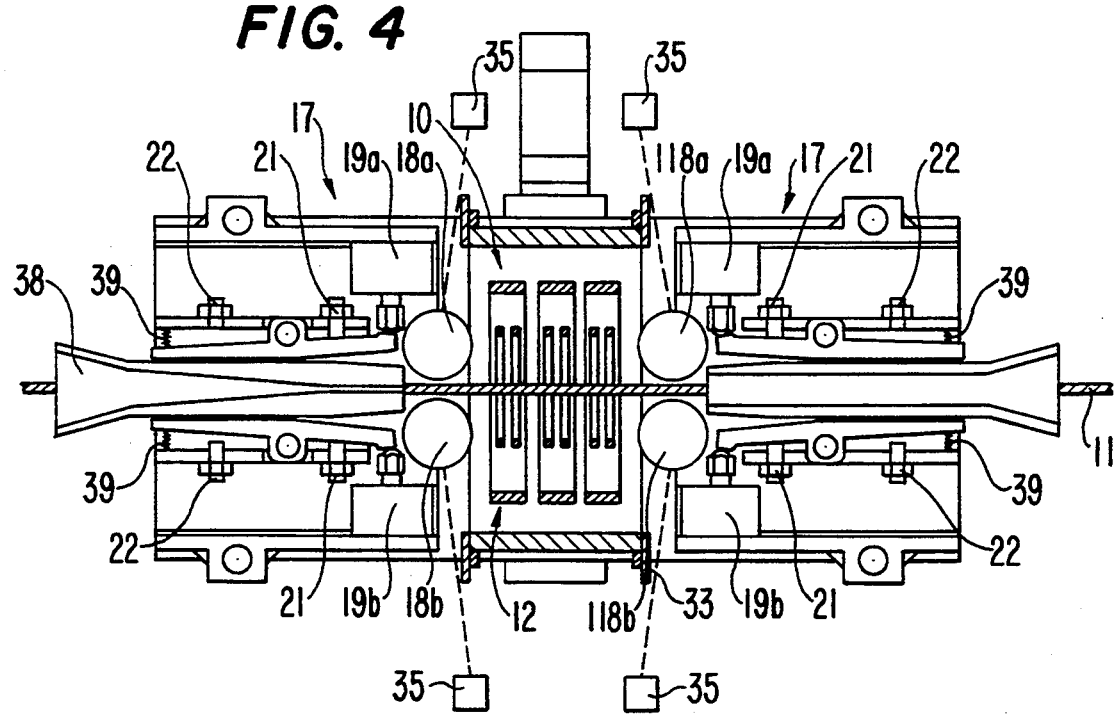
FIG. 4 is a partly cutaway plan view of the fault detection device cooperating with a means which clamps laterally and guides the bar being fed.

The detection device 10 according to the invention cooperates advantageously with a means 17 which clamps laterally and guides the bar 11 being fed (FIG. 4).

This lateral clamping and guide means 17 consists in this case of two pairs of idler rolls 18 and 118, the pairs being positioned respectively upstream and downstream of the fault detection device 10.

Each roll 18a, 18b, 118a, and 118b is actuated by its own actuator 19, which is a pneumatic actuator in this case.

These actuators 19a–19b enable the rolls 18a, 18b, 118a, 118b to be moved from an intake position to an inspect ion position, in which the rolls 18a, 18b, 118a, 118b are brought into contact with the bar.

The idler rolls 18a, 18b, 118a, 118b in the intake position are positioned initially at a given distance apart so as to determine an intake path for the feed of the bar 11. This intake path is defined substantially by rough alignment lead-in means 38.

As soon as the intake of the bar 11 has taken place, the idler rolls 18a, 18b, 118a, 118b are brought into contact with the bar 11 in the inspection position and take or by friction a peripheral speed almost the same as the linear speed of feed of the bar 11.

According to a variant the rolls 18a, 18b, 118a, 118b, before coming into contact with the bar 11 being fed, are set in rotation by suitable motors 35 at a peripheral speed almost the same as the linear speed of feed of the bar 11.

In this way the initial contact between the bar 11 and the rolls 18a, 18b, 118a, 118b is made less abrupt and any problems of wear and deterioration are lessened.

This positioning is opposed by suitable resilient means 39, which make possible a return to the intake position as soon as the step of surface inspection the bar 11 has ended and the action of the actuators 19 has ceased.

The clamping and guide means 17 is provided with position restricting means 21 and 22, which can be re-set according to the diameter of the bar 11 being processed.

In particular, the restricting means 21 limit the intake position of the rolls 18a, 18b, 118a, 118b, whereas the restricting means 22 limit the inspection position of the rolls 18a, 18b, 118a, 118b.

According to a variant the clamping and guide means 17 according to the invention arranges that the rolls 18a, 18b, 118a, 118b are not brought against the bar 11 with the same value of pressure. For instance, the rolls 18a, 18b, 118a, 118b can be characterised as being high pressure rolls 18a and 118a and low pressure rolls 18b and 118b respectively.

In this case the actuators 19 can be defined as high pressure actuators 19a and low pressure actuators 19b respectively.

In this situation the high pressure rolls 18a–118a are the first to be brought into contact with the bar 11 so as to fix the position of one side of the bar 11 in a definite manner. This position will be calculated as being the best to ensure the highest efficiency of the fault detection device 10.

Thereafter the low pressure rolls 18b–118b are brought against the bar 11.

The low pressure rolls 18b–118b are positioned by adapting themselves to the changes in diameter determined by the processing tolerance of the bar 11 and also ensure a constant pressure applied by the pairs of guide rolls 18a, 18b, 118a, 118b against the bar 11 so as to maintain conditions of maximum efficiency of the detection device 10.

Moreover, this control with a differentiated pressure makes possible a corrective action to compensate the play due to wear on the rolls 18a, 18b, 118a, 118b with a less frequent cadence and also makes possible a reduced wear on the rolls 18a, 18b, 118a, 118b owing to the constant control of the pressure.

Figure 5:
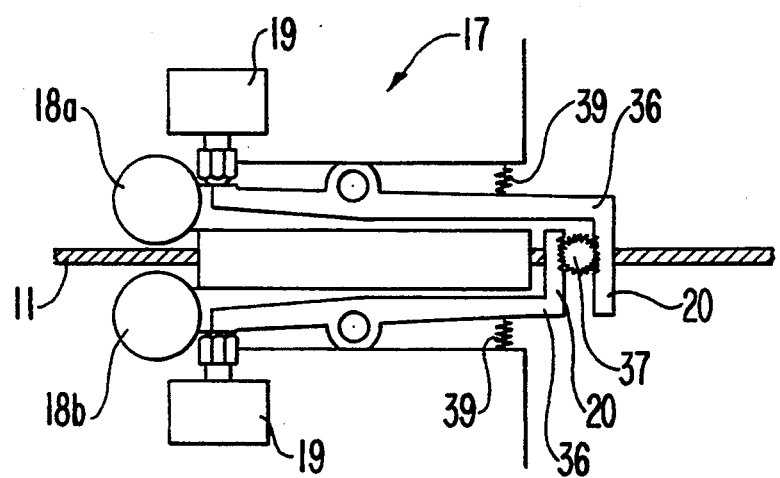
FIG. 5 is a diagrammatic plan view of a possible variant of the bar clamping means according to the invention.

According to a variant shown in the diagram of FIG. 5 the rolls 18–118 are brought against the bar 11 with analogous values of pressure and are equipped with self-alignment means to make exact the coaxial positioning of the axis of feed of the bar 11 and the axis of the detection device 10.

In this example the self-alignment means consist of levers 36 bearing on their ends two racks 20 which cooperate with one alignment pinion 37.

The idea of the solution of this invention includes devices 10 which comprise two, four or more measurement assemblies 12.

The choice of the number of measurement assemblies to be installed depends substantially on the maximum or minimum dimension of the diameters of the bar 11 being processed and on the question of a compromise between the required sensitiveness and the cost and complexity of the embodiment in question and of maintenance of the device 10.

I claim:

1. A fault detection device to detect surface faults in a hot metallic bar or wire rod travelling along a nominal feed axis at speeds up to 130 meters per second, comprising:

a pair of lateral clamping and guide rolls able to move between a first intake position in which the rolls are spaced a predetermined distance apart and a second inspection position in which the rolls are in contact with and guide the bar or rod; and, downstream of the pair of lateral clamping and guide rolls, at least two measurement assemblies, each of said at least two measurement assemblies comprising first coil and at least a pair of second coils, the first coils generating an alternating magnetic flow which causes on the surface of the bar or rod parasitic currents that generate in the second coils a magnetic feedback flow, the first and second coils lying on the same axis, the at least two measurement assemblies having their lengthwise axes able to move from an open position defining an intake hole, to an inspection position defining a resulting inspection hole, wherein the lengthwise axes of the measurement assemblies coincide substantially with the nominal feed axis when the measurement assemblies are in the open position and wherein the lengthwise axes of the measurement assemblies are substantially parallel to the nominal feed axis and are positioned substantially at an equal distance apart on about a circumference, said each measurement assembly further includes externally a rotation pivot having its axis substantially parallel to the nominal feed axis, the rotation pivots being symmetrically arranged substantially along the circumference, each said measurement assembly being pivotable around its rotation pivot between said open and said inspection position, a center of the circumference lying substantially on the nominal feed axis, when the measurement assemblies are in the inspection position, wherein an index of filling of the resulting inspection hole is greater than 0.8, the index of filling being defined by a ratio between a cross-sectional area of the bar or rod and an area of the resulting inspection hole.

2. Fault detection device as in claim 1, which comprises a second pair of lateral clamping and guide rolls downstream and in the vicinity of a last of said at least two measurement assemblies.

3. Fault detection device as in claim 1, in which at least one roll is associated with a motor.

4. Fault detection device as in claim 1, in which one roll is associated with a high pressure actuator, whereas the other roll is associated with a low pressure actuator.

5. Fault detection device as in claim 1, in which the rolls are associated with levers extending on a plane containing substantially the axis of the bar.

6. Fault detection device as in claim 5, in which the levers bear at their ends rack means with alignment pinions.

7. Fault detection device as in claim 1, in which the clamping and guide rolls include position restricting means associated with the first intake position and position restricting means associated with the second inspection position.

8. Fault detection device as in claim 1, wherein each measurement assembly further comprises a contract element opposed to said rotation pivot and cooperating with a thrust edge on a rotary drum enclosing the measurement assemblies and the respective rotation pivots, the rotary drum having a first open position and a second inspection position.

9. Fault detection device as in claim 8, in which the rotary drum is associated with guide wheels, resilient spring means and jack means, means to adjust rotation being included.

10. Fault detection device as in claim 1, wherein said index of filing is 0.95 or more.

* * * * *